United States Patent [19]

Rolland et al.

[11] Patent Number: 4,970,301
[45] Date of Patent: Nov. 13, 1990

[54] 2-(PIPERAZINYL)-2-OXOETHYLENE-SUBSTITUTED FLAVONOID COMPOUNDS

[75] Inventors: Yves Rolland, Vanves; Jacques DuHault, Croissy s/Seine, both of France

[73] Assignee: Adir et Cie, Neuilly-sur-Seine, France

[21] Appl. No.: 277,689

[22] Filed: Nov. 29, 1988

[30] Foreign Application Priority Data

Dec. 1, 1987 [FR] France .................. 87 16619

[51] Int. Cl.[5] .................. A61K 31/70; C07H 17/04
[52] U.S. Cl. .......................... 536/8; 514/870; 514/930
[58] Field of Search .............. 536/8; 514/25, 27, 870, 514/930

[56]     References Cited
       U.S. PATENT DOCUMENTS

| | | | |
|---|---|---|---|
| 3,878,191 | 4/1975 | Fukumoto et al. | 536/8 |
| 4,238,483 | 12/1980 | Frazier | 536/8 |
| 4,255,563 | 3/1981 | Wakihira et al. | 536/8 |
| 4,529,729 | 7/1985 | Regnier et al. | 514/253 |
| 4,617,293 | 10/1986 | Wahlig et al. | 514/41 |
| 4,753,929 | 6/1988 | Matsumoto et al. | 536/8 |

Primary Examiner—Ronald W. Griffin
Attorney, Agent, or Firm—Gordon W. Hueschen

[57]        ABSTRACT

Compound of general formula I:

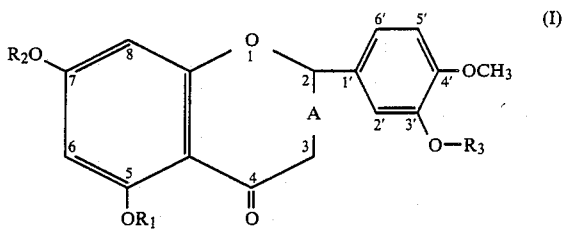

in which:

A is a single or double bond, $R_1$ and $R_3$, which may be identical or different, are each a hydrogen atom, an alkoxycarbonylmethylene radical of formula $-CH_2CO_2R_4$ (in which $R_4$ denotes an alkyl radical having 1 to 5 carbon atoms) or a radical of formula W:

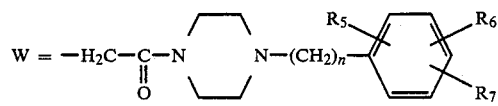

(in which n is equal to 0 or 1 and $R_5$, $R_6$ and $R_7$, which may be identical or different, are each a hydrogen or halogen atom, a hydroxyl radical, a trifluoromethyl radical, a lower alkyl radical containing 1 to 5 carbon atoms or an alkoxy radical containing 1 to 5 carbon atoms), $R_2$ is a hydrogen atom, an alkoxycarbonylmethylene radical of formula $-CH_2CO_2R_4$, a radical of formula W, or a β-glucose or rutinose molecule linked to the oxygen to which it is attached with a glycoside bond, on condition, however, that at least either $R_1$ or $R_2$ or $R_3$ always denotes a radical of formula W, and their addition salts with a pharmaceutically acceptable inorganic or organic acid.

9 Claims, No Drawings

2-(PIPERAZINYL)-2-OXOETHYLENE-SUBSTITUTED FLAVONOID COMPOUNDS

The present invention relates to new 2-(piperazinyl)-2-oxoethylene-substituted flavonoid compounds to processes for preparing them and to pharmaceutical compositions containing them.

It is already known that flavonoids and some of their semisynthetically produced derivatives possess considerable physiological and therapeutic activity: in particular, they reduce capillary fragility and/or permeability and have an anti-inflammatory action (Burger's Medicinal Chemistry, 4th Ed., Part III, p. 1258–1259 Manfred Wolff ed., J. Wiley, N.Y.) (French Patent Applications Nos. 7,329,235 and 2,183,612; U.S. Pat. No. 3,810,896).

Other compounds endowed with coronarodilatory properties are also described (U.S. Pat. No. 3,002,979). Finally, a few semisynthetic hesperetin compounds are known and find their applications in the science of food and dietetics (U.S. Pat. No. 3,976,790).

The applicant has now discovered that some 2-(piperazinyl)-2-oxoethelene-substituted flavonoid compounds, of novel structure, are endowed with very advantageous pharmacological properties. In effect, the compounds of the present invention act on biochemical mediators involved in disorders due to venous insufficiency. In addition, during in vivo trials, the products of the invention showed a very substantial inhibitory effect with respect to the formation of edema.

The subject of the present invention is more especially the 2-(piperazinyl)-2-oxoethylene-substituted flavonoid compounds of formula I:

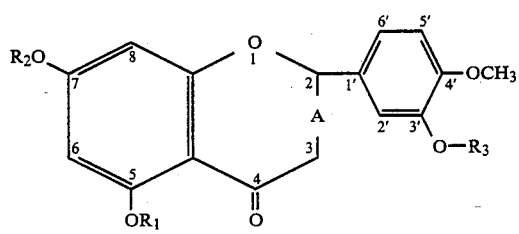

in which:
A denotes a single or double bond,
$R_1$ and $R_3$, which may be identical or different, each denote a hydrogen atom, an alkoxycarbonylmethylene radical of formula $—CH_2CO_2R_4$ (in which $R_4$ denotes an alkyl radical having 1 to 5 carbon atoms) or a radical of formula W:

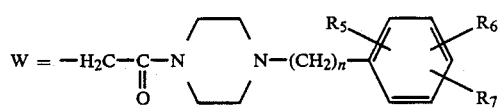

(in which n is equal to 0 or 1 and $R_5$, $R_6$ and $R_7$, which may be identical or different, each denote a hydrogen or halogen atom, a hydroxyl radical, a trifluoromethyl radical, a lower alkyl radical containing 1 to 5 carbon atoms or an alkoxy radical containing 1 to 5 carbon atoms),
$R_2$ denotes a hydrogen atom, an alkoxycarbonylmethylene radical of formula $—CH_2CO_2R_4$, a radical of formula W, or a β-glucose or rutinose molecule linked to the oxygen to which it is attached with a glycoside bond,
on condition, however, that at least either $R_1$ or $R_2$ or $R_3$ always denotes a radical of formula W,
and their addition salts with a pharmaceutically acceptable inorganic or organic acid.

The subject of the present invention is also the process for preparing compounds of general formula I, wherein:

<blockquote>either:</blockquote> diosmine, the compound of formula II:

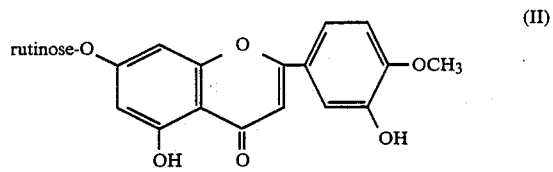

is reacted with an alkyl chloride of formula III containing the compounds of general formulae IIIa and IIIb:

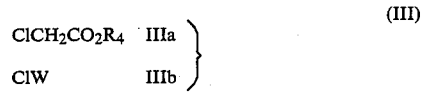

in which $R_4$ and W have the same meanings as for the formula I, in a polar nitrogenous organic solvent, in the presence of an acidic inorganic salt of an alkali metal, at a temperature of between 80° and 120° C.,
either to obtain,
with the compounds of formula IIIa, the compounds of general formula IV:

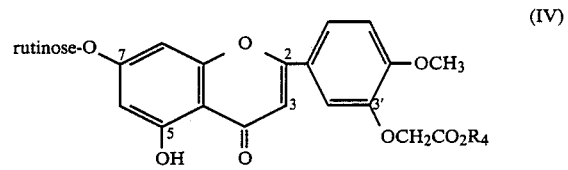

in which $R_4$ has the meaning stated above for the formula I,
which is subjected to an acid hydrolysis in the presence of a concentrated inorganic acid and at a temperature of between 35° and 55° C. to form the compound of the formula V:

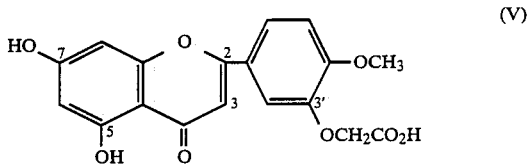

which is then:
either:
subjected to an acetylation by means of acetic anhydride in a basic nitrogenous organic solvent and at room temperature to form the compound of formula VI:

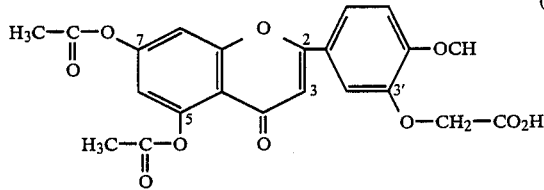

(VI)

which is reacted with a piperazine derivative of general formula VII:

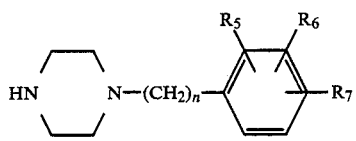

(VII)

in which n, $R_5$, $R_6$ and $R_7$ have the same meaning as for the formula I, in the presence of a low molecular weight tertiary amine and ethyl chloroformate, at a temperature of between 0° and 20° C., to form the compounds of general formula VIII:

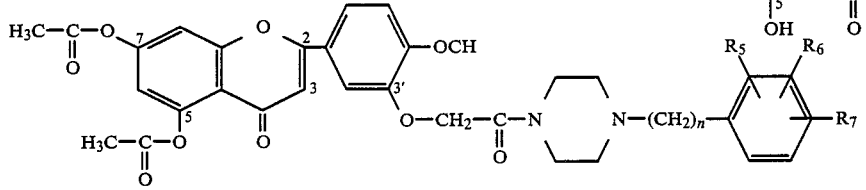

(VIII)

in which n, $R_5$, $R_6$ and $R_7$ have the meaning stated above, which is then subjected to a deacetylation in solution in dimethylformamide in the presence of an acidic inorganic salt of an alkali metal at a temperature of between 80° and 120° C., to form the compounds of general formula $I_A$:

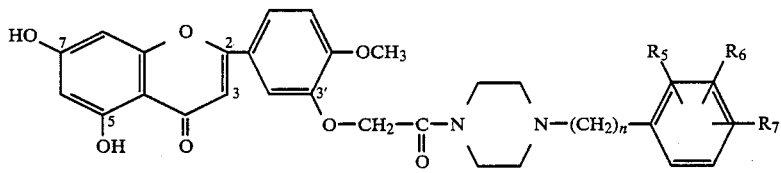

($I_A$)

in which the meaning of n, $R_5$, $R_6$ and $R_7$ remains identical to that given above, which is condensed with a compound of general formula III to form compounds of general formula $I_B$:

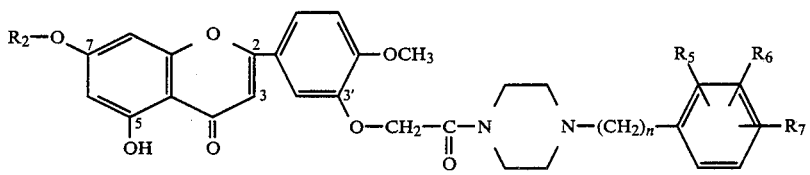

($I_B$)

in which n, $R_5$, $R_6$ and $R_7$ have the meaning stated above and $R_2$ denotes an alkoxycarbonylmethylene radical of the formula $-CH_2CO_2R_4$ or a radical of formula W, or:

esterified with a primary or secondary alcohol containing from 1 to 5 carbon atoms, in an anhydrous medium at a temperature of between 80° and 110° C. and in the presence of p-toluenesulfonic acid, to form the compounds of general formula IX:

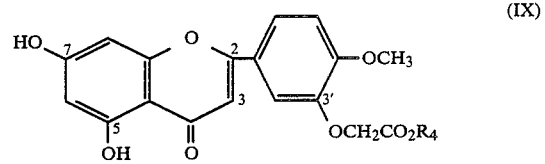

(IX)

in which $R_4$ has the same meaning as for the formula IV, which is reacted either with an alkyl chloride of general formula IIIb to form the compounds of general formula $I_C$:

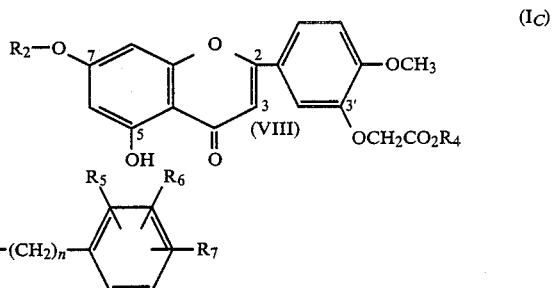

($I_C$)

in which $R_2$ denotes a radical of formula W, or with an alkyl chloride of formula IIIa to form the compounds of general formula X:

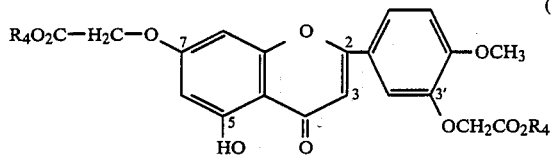

in which R₄ has the meaning stated above for the formula I,
which is condensed with the compound of general formula IIIb to obtain the compounds of general formula $I_D$:

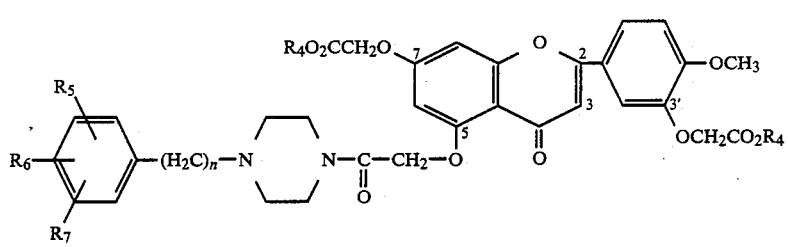

in which the meaning of n, R₄, R₅, R₆ and R₇ remains identical to that given above,
or to obtain,
with the compounds of formula III$_b$, the compounds of general formula $I_E$,

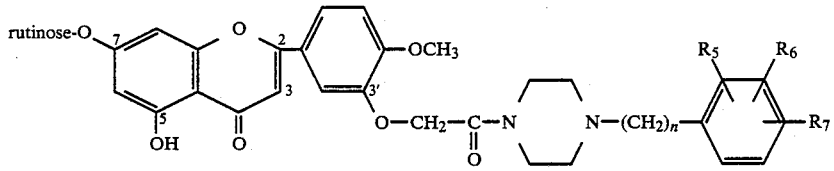

in which n, R₅, R₆ and R₇ have the meaning stated for the formula I,
which is then subjected to an enzymatic hydrolysis by means of naringinase to form the compounds of general formula $I_F$:

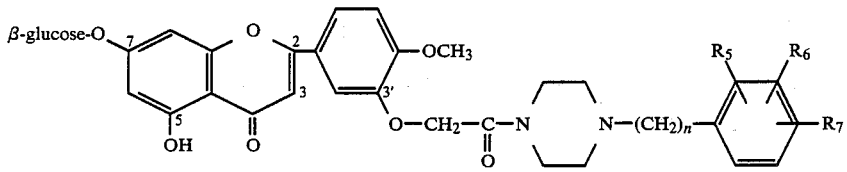

in which n, R₅, R₆ and R₇ have the meaning stated above for the formula I,
which are then, subjected to an enzymatic hydrolysis by means of β-glucosidase to form the compounds of general formula $I_A$,
which are then condensed with a compound of general formula III to form the compounds of general formula $I_B$, or:

a compound of general formula XI:

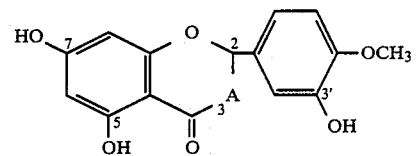

in which A has the same meaning as for the formula I, is reacted with a suitable amount of the compounds of the general formula IIIb, to form the compounds of general formula $I_G$:

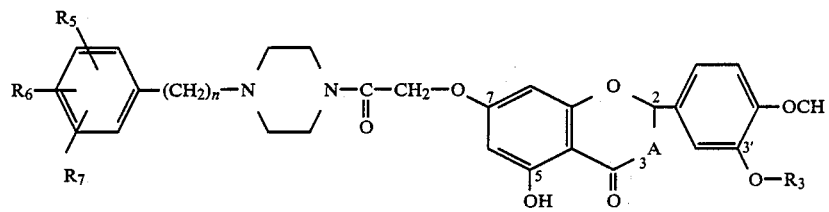

n which A, n, R₅, R₆ and R₇ have the meaning stated in the general formula I, and R₃ denotes a hydrogen atom when the amount of the compounds of general formula IIIb used is approximately equimolar, or a radical of the formula W when the alkylation is performed with at least double the amount of alkyl chloride of general formula IIIb, and wherein the compounds of the formulae $I_A$ to $I_G$, which collectively form the compounds of the formula I, are then salified, if desired, with a pharmaceutically acceptable organic or inorganic acid.

Among pharmaceutically acceptable acids for the preparation of addition salts with the compounds of general formula I, there may be mentioned hydrochloric, phosphoric, fumaric, citric, oxalic, sulfuric, ascorbic, tartaric, maleic, mandelic, methanesulfonic acids, and the like.

The compounds of general formula IIIb may be prepared by amidation of the piperazine compounds of general formula VII by means of chloroacetyl chloride. This reaction is carried out in a chlorinated organic solvent such as dichloromethane, at a temperature of between 0° and 20° C.

The compounds of the present invention possess highly advantageous pharmacological and biological properties. Furthermore, their addition salts are very water-soluble. They may hence be advantageously employed for the preparation of injectables.

The various tests performed in vivo showed that the compounds of the invention possess a very powerful anti-edematous activity. It has also been discovered from in vitro tests that the compounds of the invention exhibit highly advantageous protective effects with respect to the inflammatory reaction.

It is known that oxygen metabolites are involved in tissue inflammation reactions, both at vascular level and as regards the attack at tissue and cell level. [Bruce et al, Lab. Invest., 1982, 47, (5), p. 412–426]. Pharmacological trials carried out with the compounds of the invention proved that the latter inhibited the generation of oxygen-containing free radicals in the extracellular medium. The results of the pharmacological studies also demonstrated that the compounds of the invention possess an inhibitory activity with respect to the degredation of cyclic AMP and, like other phosphodiesterase inhibitors (Lehmeyer J. E. Johnston, R. B. Clin. Immunol. Immunopathol., 1978, 9 p. 482–490), induce a decrease in the release of mediators of the inflammatory reaction by polymorphonuclear leukocytes.

Edema and tissue inflammation are manifestations of venous insufficiency [Arch. Int. Pharmacodyn. Ther., (1981), 254, p.168; and Phlebology 85, Nergus D. and Jantet G., Ed. 1981, Libbey J., Lon. Par.].

The compounds of the present invention hence find their application in the treatment of various vascular conditions and especially for functional and organic chronic venous insufficiency of the lower limbs, of edema of the lower limbs, hemorrhoidal disease, and the like.

The compounds of the invention are substances of very low toxicity. In effect, the $LD_{50}$ observed in rats and mice after oral administration is greater than 1,600 mg.kg$^{-1}$.

The invention also extends to the pharmaceutical compositions containing, as active principal, at least one compound of general formula I, or one of its salts with a pharmaceutically compatible inorganic or organic acid, in combination with one or more inert and suitable excipients.

The pharmaceutical compositions thereby obtained are advantageously presented in various forms such as, for example, tablets, dragees, hard gelatin capsules, ointments or other pharmaceutical preparations suitable for local administration, suppositories, injectable solutions or solutions to be taken by mouth.

The dosage can vary widely according to the patient's age and weight, the nature and severity of the condition and also the administration route. Generally speaking, the unit dosage will range between 50 and 500 mg, and the daily dosage, usable in human therapy, between 50 mg and 1 g.

The preferred administration route is the oral or parenteral route.

The examples which follow, given without implied limitation, illustrate the invention.

The melting points were measured according to the micro-Köfler technique.

EXAMPLE 1

7-[2-{4-[(2,3,4-Trimethoxyphenyl)methyl]-1-piperazinyl}-2-oxoethoxy]-5-hydroxy-4'-methoxy-3'-(2-ethoxy-2-oxoethoxy)flavone

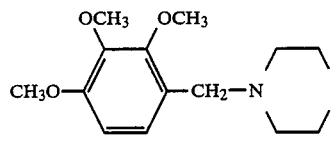
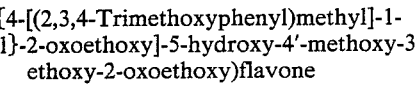
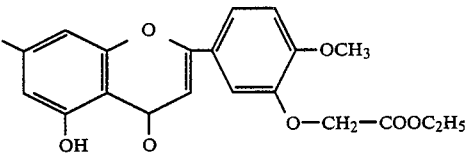

STAGE A

-3'-O-(2-Ethoxy-2-oxoethyl)diosmine 250 ml of anhydrous dimethylformamide and then 215 mmol of ethyl chloroacetate are added, under nitrogen and with stirring on an oil bath at 110° C., to 50 mmol of diosmine and 52.5 mmol of potassium hydrogen carbonate. The strongly heterogeneous reaction mixture becomes clearer with the passage of time; the reaction is continued for 3 and a half hours at 110° C. After being cooled, the reaction medium is filtered on sintered glass and evaporated to dryness in a rotary evaporator and at a vane pump to obtain a residue having a gelled appearance.

Yield: 100%.

STAGE B

3'-O-Carboxymethyldiosmetin

The residue of the preceding stage is dissolved in 300 ml of concentrated (11N) hydrochloric acid and stirred on an oil bath at 50° C.

The very dark reaction medium begins to precipitate. Crystallization is continued at room temperature, and the mixture is then filtered on sintered glass.

The precipitate is washed several times with water until the washing liquors are neutral, dried under vacuum, ground in a mortar and then dried at 50° C. at a vane pump.

Yield: 78%.

STAGE C

3'-O-(Ethoxycarbonylmethyl)diosmetin

The acid obtained in the preceding stage (14.1 g) and 0.7 g of p-toluenesulfonic acid are mixed in 200 ml of absolute ethanol; the medium is brought to reflux under nitrogen and with stirring for 5 hours at 100° C. 100 ml of ethanol are then added and the mixture is left to stand overnight at room temperature.

Yield: 89%.

1-(1-Chloroacetyl)-4-[(2,3,4-trimethoxyphenyl)methyl]-piperazine

A solution of chloroacetyl chloride (115 mmol in total) in dichloromethane is added dropwise in the course of 15 minutes to a solution, cooled in an ice bath, of 115 mmol of 4-[(2,3,4-trimethoxyphenyl)methyl]piperazine in 200 ml of dichloromethane. Stirring is continued for a further 15 minutes, and the reaction medium is then cast into ice-cold water, alkalinized to pH 8 with sodium hydrogen carbonate and extracted with dichloromethane. The organic phase is washed with water, dried over anhydrous sodium sulfate and evaporated to dryness in a rotary evaporator and then at a vane pump.

Yield: 100%.

STAGE D 50 ml of anhydrous dimethylformamide are added under nitrogen and with stirring at 110° C. to 20 mmol of 3'-O-(ethoxycarbonylmethyl)diosmetin and 30 mmol of potassium hydrogen carbonate. After dissolution of the organic compound, 24 mmol of 1-(1-chloroacetyl)-4-[(2,3,4-trimethoxyphenyl)methyl]piperazine are added. The reaction is continued for 2 hours.

After evaporation of the reaction solvent under reduced pressure, the residue obtained is solubilized in approximately 75 ml of acetone and the solution is left to crystallize. The crystals formed are isolated by filtration and then purified on a column of silica (Merck 9385 ®), using a mixture of dichloromethane and acetone (4:1 V/V) as elution solvent, to obtain pure 7-[2-{4-[(2,3,4-trimethoxyphenyl)methyl]-1-piperazinyl}-2-oxoethoxy]-5-hydroxy-4'-methoxy-3'-(2-ethoxy-2-oxoethoxy)-flavone.

Yield: 59%.

Melting point: 103°–104° C.

Elemental analysis:

|  | C | H | N |
|---|---|---|---|
| % found | 62.02 | 5.88 | 4.24 |
| % calculated | 62.42 | 5.82 | 4.04 |

Mass spectrum:

The mass spectrum was produced by chemical ionization desorption (NH₃); source temperature 175° C.; filament heating 50 to 650 mA at 7 mA/s. 693 m/z [M+H]+ (100%); 607 m/z; 525 m/z; 511 m/z; 387 m/z; 309 m/z; 267 m/z; 181 m/z.

To prepare 7-[2-{4-[(2,3,4-trimethoxyphenyl)methyl]-1-piperazinyl}-2-oxoethoxy-5-hydroxy-4'-methoxy-3'-(2-ethoxy-2-oxoethoxy)flavone monophosphate, 1 mmol of the base, dissolved in a mixture of tetrahydrofuran and dichloromethane, was salified with an equimolar amount of 1N phosphoric acid.

Solubility in water: 158 g/l.

EXAMPLE 2

5-[2-{4-[(2,3,4-Trimethoxyphenyl)methyl]-1-piperazinyl}-2-oxoethoxy-]-7,3'-bis(2-ethoxy-2-oxoethoxy)-4'-methoxyflavone

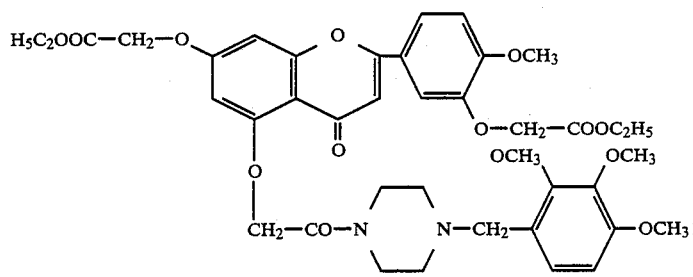

STAGE A

5-Hydroxy-7,3'-bis(2-ethoxy-2-oxoethoxy)-4'-methoxyflavone 350 ml of anhydrous dimethylformamide are added, under nitrogen and with stirring at 110° C., to 100 mmol of 3'-O-(ethoxycarbonylmethyl)diosmetin and 120 mmol of potassium hydrogen carbonate. After dissolution of the organic compound, 400 mmol of ethyl chloroacetate are added. The reaction is continued for 3 hours. The reaction medium is then cooled, and crystal formation is observed. After 24 hours at room temperature, the reaction medium is diluted with water and filtered on sintered glass. The crystals are washed with ethanol and dried at a vane pump.

Yield: 90%.

STAGE B 350 ml of anhydrous dimethylformamide are added, under nitrogen and with stirring at 110° C., to 96 mmol of the dry residue obtained above and 480 mmol of potassium carbonate. After dissolution of the organic compound, 105 mmol of 1-(1-chloroacetyl)-4-[(2,3,4-trimethoxyphenyl)methyl]piperazine are added and stirring is continued for approximately 2 and a half hours. After being cooled, the reaction medium is filtered on sintered glass and evaporated to dryness. The residue is successively purified by recrystallization in ethanol, on a column of silica (Merck 9385 ®) using a mixture of dichloromethane and methanol (96:4 V/V)

as elution solvent, and then by recrystallization in methanol. Overall yield with respect to diosmine: 42%
Melting point: 86°-88° C.
Elemental analysis:

|  | C | H | N |
|---|---|---|---|
| % found | 61.24 | 6.05 | 3.82 |
| % calculated | 61.69 | 5.95 | 3.60 |

Mass spectrum:
The mass spectrum was produced by chemical ionization desorption (NH3); source temperature 175° C.; filament heating 50 to 650 mA at 7 mA/s. 779 m/z [M+H]+ (100%); 693 m/z; 613 m/z; 473 m/z; 309 m/z; 267 m/z; 181 m/z.

5-[2-{4-[(2,3,4-Trimethoxyphenyl)methyl]-1-piperazinyl}-2-oxoethoxy]-7,3'-bis(2-ethoxy-2-oxoethoxy)-4'-methoxyflavone hydrochloride was prepared by salifying the corresponding base, dissolved in dichloromethane, with an appropriate amount of 1N ethanolic hydrochloric acid.
Solubility in water: 163 g/l.

EXAMPLE 3

3'-[2-{4-[(2,3,4-Trimethoxyphenyl)methyl]-1-piperazinyl}-2-oxoethoxy]-4'-methoxy-5-hydroxyflavone 7-chamnoglucoside

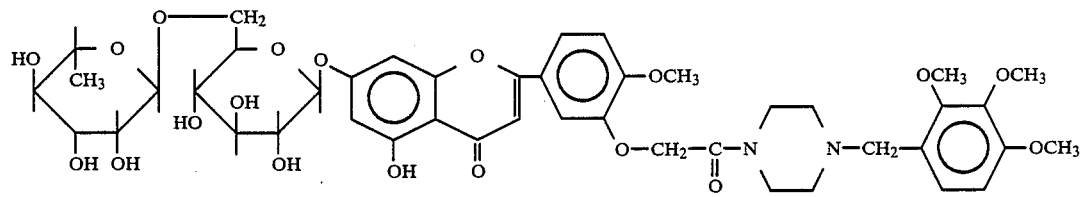

195 mmol of diosmine and 253.5 mmol of potassium hydrogen carbonate are suspended in 800 ml of anhydrous dimethylformamide under nitrogen, with stirring and at 100° C. 253.5 mmol of 1-(1-chloroacetyl)-4-[(2,3,4-trimethoxyphenyl)methyl]piperazine, dissolved in 175 ml of dimethylformamide, are then added, and the reaction is continued at this temperature for 3 hours. After being cooled, the reaction medium is filtered on sintered glass. The filtrate is diluted with water and extracted four times with ethyl acetate. The ethyl acetate is removed after decantation and the filtrate is then extracted 5 times with n-butanol saturated with water. The butanol phases, well decanted, are evaporated to dryness in a rotary evaporator. The residue is taken up with an n-butanol/water (5:1 V/V) mixture. The aqueous-alcoholic solution thereby formed is then concentrated and left overnight at room temperature. The crystals formed are recrystallized in an n-butanol/water mixture under the conditions described above, and then washed with pure n-butanol and thereafter with cyclohexane.
Yield: 65% with respect to the starting diosmine.
Melting point: 184°-186° C.
Elemental analysis:

|  | C | H | N |
|---|---|---|---|
| % found | 57.71 | 5.96 | 2.83 |
| % calculated | 57.76 | 5.95 | 3.06 |

Mass spectrum:
The mass spectrum was produced by chemical ionization desorption (NH3); source temperature 175° C.; filament heating 50 to 650 mA at 7 mA/s. 915 m/z [M+H]+; 733 m/z; 607 m/z (100%); 326 m/z; 308 m/z; 267 m/z; 181 m/z; 164 m/z; 146 m/z; 129 m/z.

3'-[2-{4-[(2,3,4-Trimethoxyphenyl)methyl]-1-piperazinyl}-2-oxoethoxy]-4'-methoxy-5-hydroxyflavone 7-chamnoglucoside hemitartrate was prepared by salifying the corresponding base, dissolved in a mixture of methanol and ethyl acetate, with an appropriate amount of 1-tartaric acid.
Solubility in water: 200 g/l.

EXAMPLE 4

3'-[2-{4-[(2,3,4-Trimethoxyphenyl)methyl]-1piperazinyl}-2-oxoethoxy]-4'-methoxy-5-hydroxyflavone 7β-glucoside

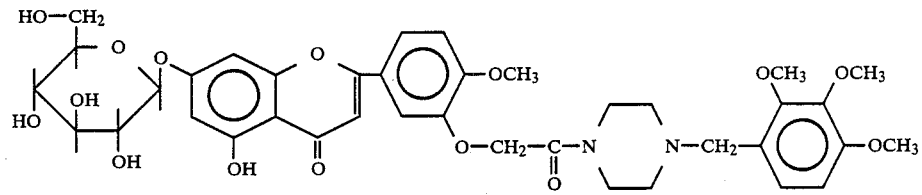

39 mmol of 3'-[2-{4-[(2,3,4-trimethoxyphenyl)methyl]-1-piperazinyl}-2-oxoethoxy -4'-methoxy-5-hydroxyflavone 7-rhamnoglucoside tartrate, the compound of Example 3, are dissolved in one liter of distilled water. The solution is adjusted to pH 4 by means of 0.5N hydrochloric acid and brought to 40° C., and 1.2 g of naringase (Sigma ® N 1385) are then added. After 2 hours' stirring at this temperature, the reaction is stopped.
The reaction medium is treated with 200 ml of dimethylformamide, transferred to a separating funnel and alkalinized with aqueous bicarbonate until precipitation is distinct. Extraction is carried out with three times 600 ml and then twice 400 ml of n-butanol saturated with water. After decantation, the butanol phases are combined and evaporated to dryness. The residue is taken up with methanol and heated under reflux until dissolution takes place. The solution thereby formed is left for 24 hours at room temperature. The crystals formed are separated by filtration and then dried at 45° C. under vacuum.
Yield: 79 %.
Melting point: 132°–134° C.
Elemental analysis:

|  | C | H | N |
|---|---|---|---|
| % found | 56.64 | 5.89 | 3.33 |
| % calculated | 56.54 | 6.03 | 3.47 |

Mass spectrum:
The spectrum was produced with a FAB source in positive mode; incident gas, krypton; energy 7 keV; matrix, glycerol. 769 m/z [M+H]+; 767 m/z 737 m/z; 607 m/z; 589 m/z; 427 m/z; 301 m/z.

3'-[2-{4-[(2,3,4-Trimethoxyphenyl)methyl]-1-piperazinyl}-2-oxoethoxy]-4'-methoxy-5-hydroxyflavone 7β-glucoside monophosphate was prepared after adding an appropriate amount of phosphoric acid to an acetone solution containing 3'-[2-{4-[(2,3,4-trimethoxyphenyl)methyl]-1-piperazinyl}-2-oxoethoxy]-4'-methoxy-5-hydroxyflavone 7β-glucoside.
Solubility in water: 43 g/l.

EXAMPLE 5

3'-[2-{4-[(2,3,4-Trimethoxyphenyl)methyl]-1-piperazinyl}-2-oxoethoxy]-4'-methoxy-5,7-dihydroxyflavone

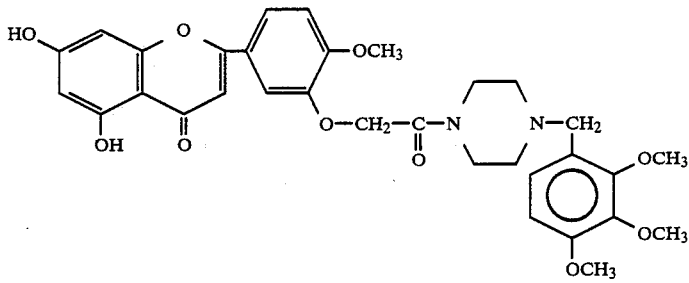

PROCESS A 20 mmol of the compound of Example 4 are stirred in 300 ml of a mixture of acetone and water (V/V) at room temperature. 20 ml of normal aqueous phosphoric acid solution and 200 ml of water are then added. The mixture is stirred on a water bath until dissolution is complete, and is then concentrated in a rotary evaporator until the acetone has distilled off completely. The residual aqueous solution of pH 3.5 is diluted with water to achieve a final volume of 1 liter and a pH of 3.95, and is then brought to 37° C. 550 mg of β-glucosidase (Sigma ® type II G 8625, 7.1 u/mg) are then added, and the reaction is left to proceed at this temperature with stirring for 48 hours.

The reaction mixture is brought to pH 7 by adding aqueous bicarbonate and then extracted with aqueous n-butanol (800 ml, 400 ml, 300 ml). The combined butanol phases are clarified by passage through celite and, after a further decantation, are evaporated to dryness.

The residue is purified on a column of silica (Merck ® 9385), using a mixture of dichloromethane and acetone (V/V) as elution solvent.
Yield: 77%.

PROCESS B

STAGE A 5,7-bis(O-acetyl)-3'-O-carboxymethyldiosmetin 7.5 mmol of the acid obtained in Stage B of Example 1 are solubilized by heating in 20 ml of a mixture of pyridine and acetic anhydride (V/V). The reaction mixture is left for 48 hours at room temperature, water is then added and the mixture is extracted with dichloromethane. After washing with water, drying over anhydrous sodium sulfate and filtration, a residue is recovered after evaporation, yielding, on crystallization in methanol, the pure expected product.
Yield: 60%.

STAGE B

3'-[2-{4-[(2,3,4-Trimethoxyphenyl)methyl]-1-piperazinyl}-2-oxoethoxy]-4'-methoxy--5,7-bis(acetoxy)-flavone 2 mmol of the compound obtained in the preceding stage are suspended in 60 ml of dichloromethane in an ice bath. 2 mmol of triethylamine and 2 mmol of ethyl chloroformate are then added. After 40 minutes at 0° C., 2 mmol of 4-[(2,3,4-trimethoxyphenyl)methyl]piperazine are added. The reaction medium is stirred for 45 minutes at room temperature, and it is then washed and evaporated to dryness to obtain the expected compound.

STAGE C

The compound obtained in the preceding stage s solubilized in 40 ml of dimethylformamide and stirred at 100° C. under nitrogen in the presence of 6 mmol of potassium hydrogen carbonate for 4 hours. After being cooled, the medium is filtered and evaporated to dryness to give the expected compound.
Overall yield: 40%
Melting point: 200°–202° C.
Elemental analysis:

|  | C | H | N |
|---|---|---|---|
| % found | 63.41 | 5.63 | 4.59 |
| % calculated | 63.36 | 5.65 | 4.62 |

Mass spectrum:
The mass spectrum was produced by chemical ionization desorption (NH3); source temperature 160° C.; filament intensity 250 uA. 607 m/z [M+H]+; 441 m/z; 427 m/z; 425 m/z; 309 m/z; 307 m/z; 301 m/z; 267 m/z; 181 m/z.

The corresponding methanesulfonate was prepared by salification of 3'-[2-{4-[(2,3,4-trimethoxyphenyl)methyl]-1-piperazinyl}-2-oxoethoxy]-4'-methoxy-5,7-dihy-

EXAMPLE 7

7,3'-Bis[2-{4-[(2,3,4-trimethoxyphenyl)methyl]-1-piperazinyl}-2-oxoethoxy]-5-hydroxy-4'-methoxyflavone

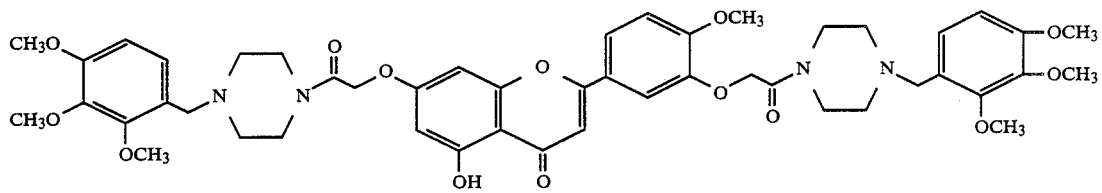

15 ml of anhydrous dimethylformamide are added, under nitrogen and with stirring at 110° C., to 5 mmol of the compound of Example 5 and 6 mmol of potassium hydrogen carbonate. 6 mmol of 1-(1-chloroacetyl)-4-[(2,3,5-trimethoxyphenyl)methyl]piperazine, dissolved in dimethylformamide, are then added, and the reaction is continued for 3 hours. After being cooled, the reaction medium is filtered, evaporated to dryness and then purified by chromatography on a silica column (Merck ® 9385), using a mixture of acetone and dichloromethane (2:1 V/V) as elution solvent.

Yield: 60%.

Elemental analysis:

|  | C | H | N |
|---|---|---|---|
| % found | 61.25 | 6.05 | 5.85 |
| % calculated* | 61.30 | 6.33 | 5.96 |

*corrected for 3% H₂O

Mass spectrum:

The mass spectrum was obtained with a positive FAB source; incident gas, krypton; energy 7 eV; matrix, glycerol 913 m/z [M+H]+; 733 m/z; 607 m/z.

7,3'-Bis[2-{4-[(2,3,4-trimethoxyphenyl)methyl]-1-piperazinyl}-2-oxoethoxy]-5-hydroxy-4'-methoxyflavone biphosphate was prepared by salification of the corresponding base, dissolved in an acetone/water mixture, with phosphoric acid.

Solubility in water: 221 g/l.

--- droxyflavone, dissolved in a mixture of tetrahydrofuran and water, with methanesulfonic acid.

Solubility in water: 35 g/l.

EXAMPLE 6

3'-[2-{4-[(2,3,4-Trimethoxyphenyl)methyl]-1-piperazinyl}-2-oxoethoxy]-4'-methoxy-5-hydroxy-7-(2-ethoxy-2-oxoethoxy)flavone

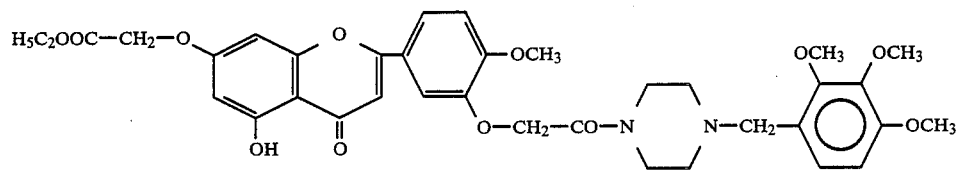

15 ml of anhydrous dimethylformamide are added under nitrogen to 5 mmol of the compound of Example 5 and 5.25 mmol of potassium hydrogen carbonate, and the mixture is heated with stirring to 110° C. after dissolution of the compound of Example 5, 20 mmol of ethyl chloroacetate are added and the reaction is continued for 2 hours. After being cooled, the reaction medium is filtered and evaporated to dryness. The residue is then recrystallized in ethanol to give the expected product.

Yield: 60%.

Melting point: 105°–106° C.

Elemental analysis:

|  | C | H | N |
|---|---|---|---|
| % found | 62.03 | 5.90 | 3.96 |
| % calculated | 62.42 | 5.82 | 4.04 |

Mass spectrum:

The mass spectrum was produced by chemical ionization desorption (NH₃); source temperature 175° C.; filament heating 50 to 650 mA at 7 mA/s. 693 m/z [M+H]+; 511m/z; 267 m/z; 181 m/z.

3'[2-{4-[(2,3,4-Trimethoxyphenyl)methyl]-1-piperazinyl}-2-oxoethoxy]-4'-methoxy-5-hydroxy-7-(2-ethoxy-2-oxoethyoxy)flavone phosphate was prepared by adding an appropriate amount of phosphoric acid to a water/acetone solution of the corresponding base.

Solubility in water: 39.5 g/l.

EXAMPLE 8

7-[2-{4-[(2,3,4-Trimethoxyphenyl)methyl]-1-piperazinyl}-2-oxoethoxy]-5,3'-dihydroxy-4'-methoxyflavanone

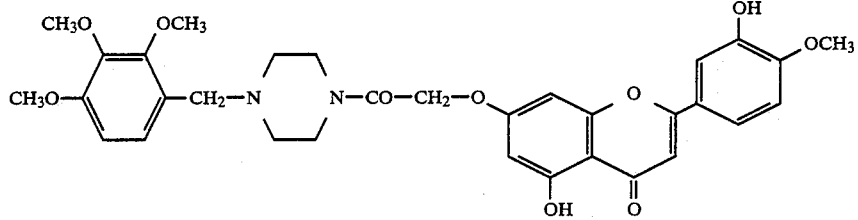

120 mmol of hesperetin are stirred in the presence of 132 mmol of potassium hydrogen carbonate in 500 ml of anhydrous dimethylformamide at 110° C. under nitrogen. After dissolution of the hesceretin, 126 mmol of 1-(1-chloroacetyl)-4-[(2,3,4-trimethoxyphenyl)methyl]-piperazine, dissolved in 100 ml of dimethylformamide, are added, and stirring is continued at 110° C. for 2 hours.

After being cooled, the reaction medium is filtered on sintered glass and evaporated to dryness.

The dry residue is dissolved in 600 ml of dichloromethane and, after being left standing for one hour at room temperature, is filtered on celite. The filtrate is then purified on a column of silica (Amicon ® 84068), using a mixture of dichloromethane and methanol (97.5:2.5 V/V) as eluant.

Yield: 49%.

Elemental analysis:

|            | C     | H    | N    |
|------------|-------|------|------|
| % found    | 62.78 | 6.07 | 4.54 |
| % calculated | 63.15 | 5.96 | 4.60 |

Mass spectrum:

The mass spectrum was obtained by chemical ionization desorption (NH3); source temperature 175° C.; filament heating 50 to 60 mA at 7 mA/s. 609 m/z [M+H]+; 325 m/z; 309 m/z; 303 m/z; 267 m/z; 181 m/z.

7-[2-{4-[(2,3,4-Trimethoxyphenyl)methyl]-1-piperazinyl}-2-oxoethoxy]-5,3'-dihydroxy-4'-methoxyflavanone methanesulfonate was prepared by adding an appropriate amount of methanesulfonic acid to a water-/acetone solution of the abovementioned base.

Solubility in water: 1.4 g/l.

EXAMPLE 9

7,3'-Bis[2-(4-benzyl-1-piperazinyl)-2-oxoethoxy]-5-hydroxy-4'-methoxyflavone

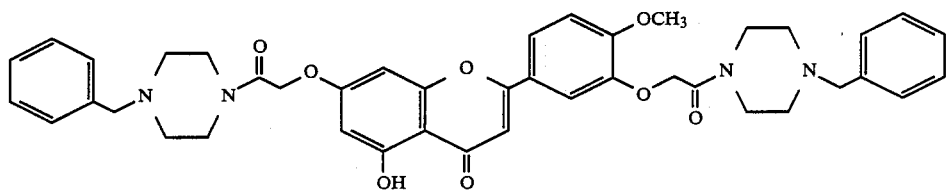

This compound was prepared according to the process described in Example 7, but using 1-(1-chloroacetyl)-4-benzylpiperazine instead of 1-(1-chloroacetyl)-4-[(2,3,4-trimethoxyphenyl)methyl]piperazine.

Yield: 25% (with respect to diosmine).

Elemental analysis:

|              | C     | H    | N    |
|--------------|-------|------|------|
| % found      | 68.65 | 5.95 | 7.20 |
| % calculated | 68.84 | 6.05 | 7.65 |

Proton nuclear magnetic resonance spectrum (400 MHz - solvent CDCl3):

2.5 ppm, m, 8H; 3.58 ppm, s, 2H; 3.6 ppm, s, 2H; 3.7 ppm, m, 8H; 4.0 ppm, s, 3H; 4.8 ppm, s, 2H; 4.87 ppm, s, 2H; 6.4 ppm, d, 1H; 6.6 ppm, t, 2H; 7.0 ppm, d, 1H; 3.32 ppm, m, 10H; 7.45 ppm, d, 1H; 7.6 ppm, d, 1H; 12.8 ppm, 1H, exchangeable).

EXAMPLE 10

3'-[2-{4-[(2-Chlorophenyl)methyl]-1-piperazinyl}-2-oxoethoxy]-4'-methoxy-5-hydroxy-7-(2-ethoxy-2-oxoethoxy)flavone

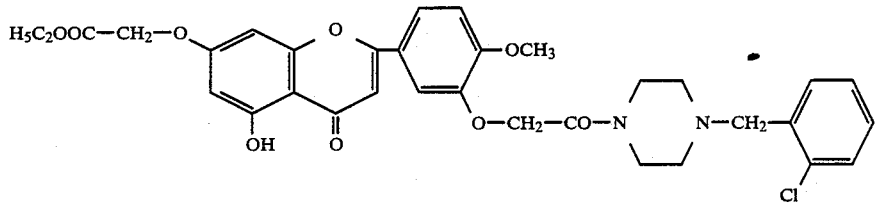

This compound was synthesized from 3'-[2-{4-[(2-chlorophenyl)methyl]-1-piperazinyl}-2-oxoethoxy]-4'-methoxy-5,7-dihydroxyflavone according to the process described in Example 6. The latter compound was obtained by the alkylation of diosmetin with 1-(1-chloroacetyl)-4-[(2-chlorophenyl)methyl]piperazine.

Yield: 27% (with respect to diosmine).

Proton nuclear magnetic resonance spectrum (400 MHz -solvent CDCl₃);

1.2 ppm, t, 3H; 2.5 to 3.58 ppm, m, 8H; 3.58 ppm, s, 2H; 3.85 ppm, s, 3H; 4.2 ppm, q, 2H; 4.62 ppm, s, 2H; 4.76 ppm, s, 2H; 6.28 ppm, d, 1H; 6.43 ppm, 1H; 6.45 ppm, s, 1H; 6.9 ppm, d, 1H; 7.15 to 7.3 ppm, m, 4H; 7.38 ppm, d, 1H; 7.45 ppm, d, 1H; 12.7 ppm, 1H, exchangeable.

EXAMPLE 11

5-[2-(4-Benzyl-1-piperazinyl)-2-oxoethoxy]-7,3'-bis(2-ethoxy-2-oxoethoxy)-4'-methoxyflavone

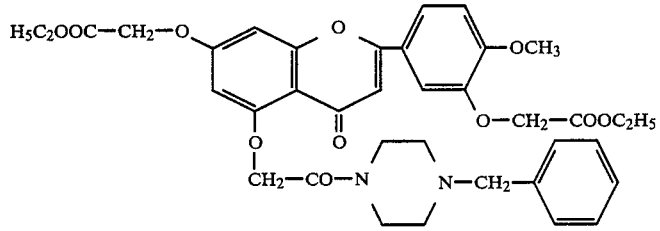

This compound was prepared according to the process described in Example 2, by condensing 5-hydroxy-7,3'-bis(2-ethoxy-2-oxoethoxy)-4'-methoxyflavone and 1-(1-chloroacetyl)-4-benzylpiperazine.

Yield: 37%.

Elemental analysis:

|  | C | H | N |
|---|---|---|---|
| % found | 64.68 | 5.62 | 3.85 |
| % calculated | 64.53 | 5.85 | 4.07 |

Proton nuclear magnetic resonance spectrum (400 MHz - solvent CDCl₃):

1.23 ppm, t, 6H; 2.35 ppm, m, 4H; 3.55 to 3.70 ppm, m, 4H; 3.42 ppm, s, 2H; 3.9 ppm, s, 3H; 4.22 ppm, q, 4H; 4.62 ppm, s, 2H; 4.70 ppm, s, 2H; 4.80 ppm, s, 2H; 6.43 ppm, s, 1H; 6.5 ppm, d, 2H; 6.92 ppm, d, 1H; 7.2 ppm, m, 5H; 7.25 ppm, d, 1H; 7.48 ppm, d, 1H.

EXAMPLE 12

5-[2-{4-[(4-Chlorophenyl)methyl]-1-piperazinyl}-2-oxoethoxy]-7,3'-bis(2-ethoxy-2-oxoethoxy)-4'-methoxyflavone

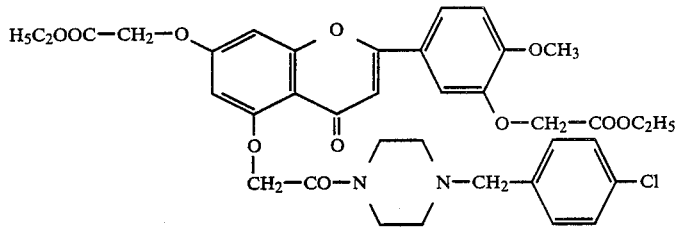

This compound was prepared according to the process described in Example 2, by condensing 5-hydroxy-7,3'-bis(2-ethoxy-2-oxoethoxy)-4'-methoxyflavone and 1-(1-chloroacetyl)-4-[(4-chlorophenyl)methyl]piperazine.

Yield: 33%.

Elemental analysis:

| % found | 61.19 | 5.20 | 3.65 | 5.23 |
|---|---|---|---|---|
| % calculated | 61.45 | 5.44 | 3.87 | 4.90 |

Mass spectrum:

The mass spectrum was obtained by chemical ionization adsorption (NH₃); source temperature 150° C.; energy 70 eV. 723 m/z [M+H]+; 637 m/z; 597 m/z; 513 m/z; 485 m/z; 473 m/z; 269 m/z; 253 m/z; 239 m/z; 211 m/z; 142 m/z; 125 m/z. Proton nuclear magnetic resonance spectrum (400 MHz - solvent CDCl₃);

1.25 ppm, t, 6H; 2.35 to 3.55 ppm, m, 4H; 2.30 to 3.70 ppm, m, 4H; 3.45 ppm, s, 2H; 3.9 ppm, s, 3H; 4.22 ppm, q, 4H; 4.60 ppm, s, 2H; 4.70 ppm, s, 2H; 4.80 ppm, s, 2H; 6.45 ppm, s, 2H; 6.5 ppm, d, 2H; 6.92 ppm, d, 1H; 7.3 ppm, d, 1H; 7.3 ppm, m, 4H; 7.48 ppm, d, 1H.

EXAMPLE 13

5-[2-{4-[(4-Methylphenyl)methyl]-1-piperazinyl}-2-oxoethoxy]-7,3'-bis(2-ethoxy-2-oxoethoxy)-4'-methoxyflavone

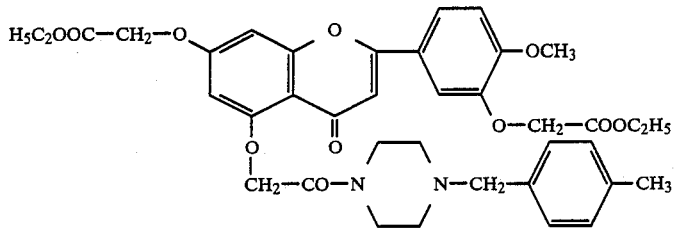

This compound was prepared according to the process described in Example 2, by condensing 5-hydroxy-7,3'-bis(2-ethoxy-2-oxoethoxy)-4'-methoxyflavone and 1-(1-chloroacetyl)-4-[(4-methylphenyl)methyl]piperazine.

Yield: 25%.

Elemental analysis:

|         | C     | H    | N    |
|---------|-------|------|------|
| % found | 64.18 | 5.67 | 3.66 |
| % calculated | 64.95 | 6.02 | 3.99 |

Proton nuclear magnetic resonance spectrum (400 MHz - solvent CDCl$_3$);

1.30 ppm, t, 6H; 2.30 ppm, s, 3H; 2.40 to 3.60 ppm, m, 4H; 2.40 to 3.75 ppm, m, 4H; 3.45 ppm, s, 2H; 3.95 ppm, s, 3H; 4.30 ppm, q, 4H; 4.70 ppm, s, 2H; 4.75 ppm, s, 2H; 4.85 ppm, s, 2H; 6.50 ppm, s, 1H; 6.60 ppm, d, 2H; 7.00 ppm, d, 1H; 7.1 ppm, m, 4H; 7.30 ppm, d, 1H; 7.55 ppm, d, 1H.

EXAMPLE 14

5-{2-(4-Phenyl-1-piperazinyl)-2-oxoethoxy}-7,3'-bis(2-ethoxy-2-oxoethoxy)-4'-methoxyflavone

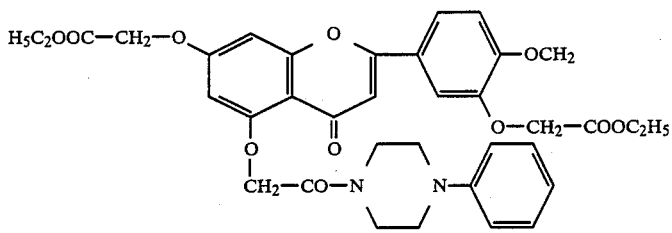

This compound was prepared according to the process described in Example 2, by condensing 5-hydroxy-7,3'-bis(2-ethoxy-2-oxoethoxy)-4'-methoxyflavone and 1-(1-chloroacetyl)-4-phenylpiperazine.

Yield: 30%.

Elemental analysis:

|         | C     | H    | N    |
|---------|-------|------|------|
| % found | 63.79 | 5.37 | 4.09 |
| % calculated | 64.09 | 5.68 | 4.15 |

Proton nuclear magnetic resonance spectrum (400 MHz - solvent CDCl$_3$);

1.3 ppm, t, 6H; 3.15 to 3.75 ppm, m, 4H; 3.15 to 3.95 ppm, m, 4H; 3.95 ppm, s, 3H; 4.3 ppm, q, 4H; 4.6 ppm, s, 2H; 4.65 ppm, s, 2H; 4.90 ppm, s, 2H; 6.50 ppm, d 1H; 6.55 ppm, d, 1H; 6.65 ppm, d, 1H; 6.85 to 7.20 ppm, m, 5H; 7.0 ppm, d, 1H; 7.3 ppm, d, 1H; 7.55 ppm, d, 1H.

EXAMPLE 15

7-[2-{4-[(4-Chlorophenyl)methyl]-1-piperazinyl}-2-oxoethoxy]-5-hydroxy-4'-methoxy-3'-(2-ethoxy-2-oxoethoxy)flavone

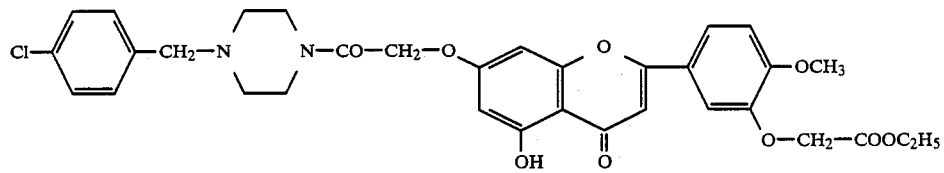

This compound was prepared by condensing 3'-O-(ethoxycarbonylmethyl)diosmetin and 1-(1-chloroacetyl)-4-[(4-chlorophenyl)methyl]piperazine according to the process described in Example 1.

Yield: 84%.

Elemental analysis:

|         | C     | H    | N    | Cl   |
|---------|-------|------|------|------|
| % found | 62.02 | 5.16 | 4.38 | 5.62 |
| % calculated | 62.22 | 5.22 | 4.40 | 5.56 |

Proton nuclear magnetic resonance spectrum (400 MHz - solvent CDCl$_3$):

1.23 ppm, t, 3H; 2.45 to 3.60 ppm, m, 4H; 2.45 to 3.65 ppm, m, 4H; 3.50 ppm, s, 2H; 3.85 ppm, s, 3H; 4.22 ppm, q, 2H; 4.8 ppm, s, 4H; 6.35 ppm, d, 1H; 6.55 ppm, s, 1H; 6.55 ppm, d, 1H; 7.30 ppm, m, 4H; 7.35 ppm, d, 1H; 7.60 ppm, d, 1H; 12.8 ppm, 1H; exchangeable.

EXAMPLE 16

7-[2-(4-Benzyl-1-piperazinyl)-2-oxoethoxy]-5-hydroxy-4'-methoxy-3'-(2-ethoxy-2-oxoethoxy)flavone

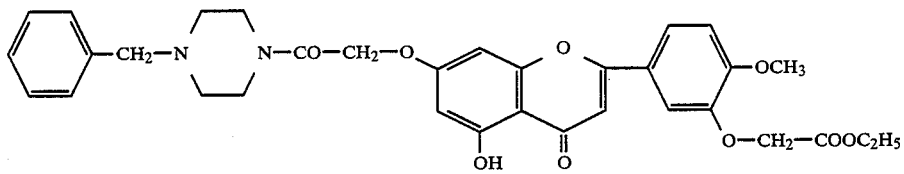

This compound was prepared by condensing 3'-O-(ethoxycarbonylmethyl)diosmetin and 1-(1-chloroacetyl)-4-benzylpiperazine according to the process described in Example 1.

Yield: 86%.

Elemental analysis:

|  | C | H | N |
|---|---|---|---|
| % found | 65.44 | 5.52 | 4.91 |
| % calculated | 65.77 | 5.69 | 4.65 |

Proton nuclear magnetic resonance spectrum (400 MHz - solvent CDCl₃):

1.30 ppm, t, 3H; 2.5 to 3.55 ppm, m, 4H; 2.5 to 3.65 ppm, m, 4H; 3.55 ppm, s, 2H; 4.0 ppm, s, 3H; 4.3 ppm, q, 2H; 4.8 ppm, s, 4H; 6.35 ppm, d, 1H; 6.55 ppm, d, 1H; 6.55 ppm, s, 1H; 7.0 ppm, d, 1H; 7.3 ppm, m, 5H; 7.35 ppm, d, 1H; 7.6 ppm, d, 1H; 12.8 ppm, 1H, exchangeable.

EXAMPLE 17

3'-[2-(4-Benzyl-1-piperazinyl)-2-oxoethoxy]-4'-methoxy-5-hydroxyflavone 7-rhamnoglucoside

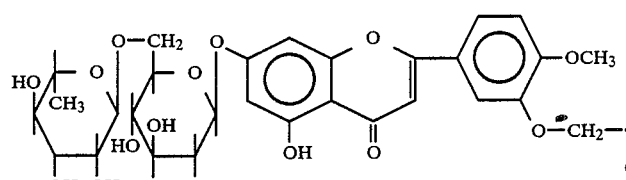

This compound was prepared from diosmine and 1-(1-chloroacetyl)-4-benzylpiperazine according to the process described in Example 3.

Yield: 70%.

Melting point: 214°–217° C.

Elemental analysis:

|  | C | H | N |
|---|---|---|---|
| % found | 59.63 | 5.98 | 3.38 |
| % calculated | 59.70 | 5.87 | 3.40 |

Mass spectrum:

The spectra were produced with an FAB source in positive and negative mode; incident gas krypton; energy, 8 keV; matrix, glycerol/thioglycerol (1:1). FAB⁺: 825 m/z [M+H]⁺; 823 m/z; 733 m/z; 679 m/z; 661 m/z; 517 m/z; 91 m/z. FAB⁻: 824 m/z [M].⁻; 823 m/z; 809 m/z; 663 m/z; 621 m/z; 607 m/z; 515 m/z; 299 m/z.

EXAMPLE 18

3'-[2-{4-[(2-Chlorophenyl)methyl]-1-piperazinyl}-2-oxoethoxy]-4'-methoxy-5-hydroxyflavone 7-rhamnoglucoside

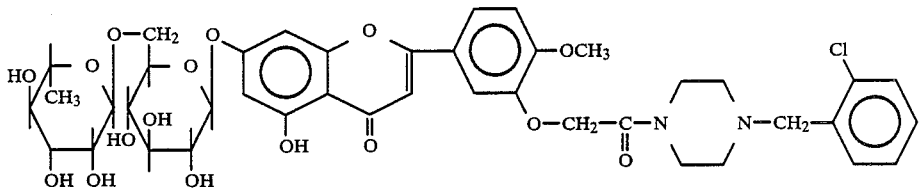

This compound was prepared from diosmine and 1-(1-chloroacetyl)-4-[(2-chlorophenyl)methyl]piperazine according to the process described in Example 3.

Yield: 64%.

Melting point: 200°–222° C.

Elemental analysis:

|  | C | H | N | Cl |
|---|---|---|---|---|
| % found | 57.42 | 5.42 | 3.14 | 4.29 |
| % calculated | 57.31 | 5.51 | 3.26 | 4.13 |

Mass spectrum:

The spectra were produced with an FAB source in positive and negative mode; incident gas krypton; energy, 8 keV; matrix glycerol/thioglycerol (1:1) FAB⁺: 859 m/z [M+H]⁺; 713 m/z; 551 m/z; 147 m/z; 125 m/z; FAB⁻: 858 m/z [M].⁻; 857 m/z; 607 m/z; 549 m/z; 299 m/z; 163 m/z.

EXAMPLE 19

3′-[2-{4-[(4-Chlorophenyl)methyl]-1-piperazinyl}-2-oxoethoxy]-4′-methoxy-5-hydroxyflavone 7-rhamnoglucoside

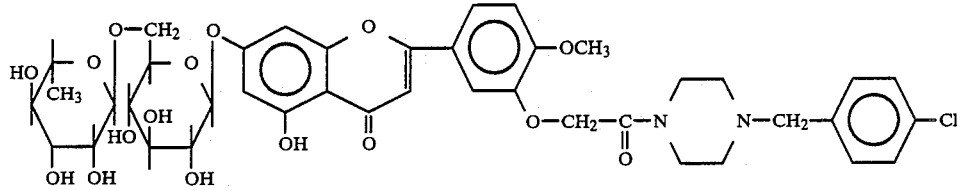

This compound was prepared according to the process described in Example 3, starting with diosmine and 1-(1-chloroacetyl)-4-[(4-chlorophenyl)methyl]piperazine.

Yield: 30%.

Mass spectrum:

The spectra were produced with an FAB source, in positive and negative mode; incident gas, krypton; energy, 8 keV; matrix, glycerol/thioglycerol (1:1). FAB+: 859 m/z [M+H]+; 857 m/z; 551 m/z; FAB−: 858 m/z [M].−; 549 m/z.

EXAMPLE 20

3′-[2-{4-[(4-Methylphenyl)methyl]-1-piperazinyl}-1-oxoethoxy]-4′-methoxy-5-hydroxyflavone 7-rhamnoglucoside

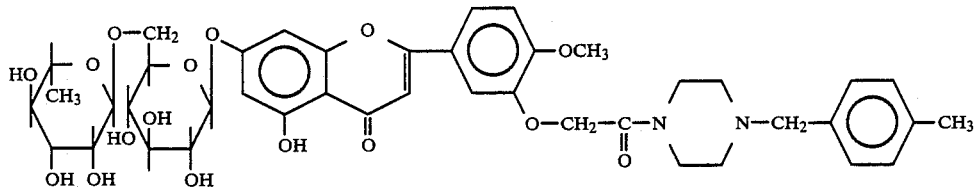

This compound was prepared according to the process described in Example 3, starting with diosmine and 1-(1-chloroacetyl)-4-[(4-methylphenyl)methyl]piperazine.

Yield: 56%.

Mass spectrum:

The spectra were produced with an FAB source, in positive and negative mode; incident gas, krypton; energy, 8 keV; matrix, diethanolamine. FAB+: 838 m/z [M+H]+; 821 m/z; 421 m/z; 316 m/z; 211 m/z; 105 m/z; FAB−: 838 m/z [M].−; 837 m/z; 529 m/z; 209 m/z.

EXAMPLE 21

3′-[2-(4-Phenyl-1-piperazinyl)-2-oxoethoxy]-4′-methoxy-5-hydroxyflavone 7-rhamnoglucoside

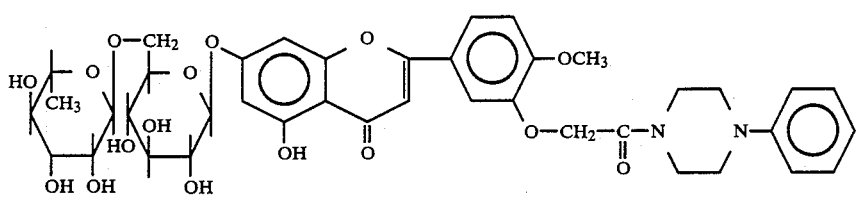

This compound was prepared by condensing diosmine with 1-(1-chloroacetyl)-4-phenylpiperazine.

Yield: 59%.

Melting point: 218°–221° C.

Elemental analysis:

|  | C | H | N |
|---|---|---|---|
| % found | 58.69 | 5.33 | 3.46 |
| % calculated | 59.25 | 5.75 | 3.45 |

Mass spectrometry:

The spectra were produced with an FAB source, in positive and negative mode; incident gas, krypton; energy, 8 keV; matrix, glycerol/thioglycerol (1:1) FAB+: 811 m/z [M+H]+; FAB−: 809 m/z; 795 m,z;

Pharmacological Study

EXAMPLE 22

Croton Oil-Induced Edema of the Mouse's Ear

This test consists in inflaming the mouse's ears with an irritant solution based on croton oil, and in testing the preventive effect of the test compounds administered per os.

The tests were carried out on batches of at least 8 CD₁ (Charles River) male mice of average weight 18–20 g. The compounds of the invention were administered by gavage with a tube, in a single dose, on the basis of 0.1 ml of liquid per 10 g of mouse. The mouse was deprived of food, but not of drink, 2 hours before the gavage and until after the irritation.

Thirty minutes after the gavage, each mouse was lightly anesthetized with ether. 10 μl of the irritant solution were then deposited by means of an Eppendorf pipette on the cutaneous surface of the pinna of the right ear; the left ear, which was not subjected to any treatment, acted as control. The animal was then replaced in the cage and sacrificed six hours later. The ears were sectioned along the cartilagineous edge and weighed immediately.

To assess the activity of the product, the mean increase in weight of the ears of the treated batches (m) is compared by Student's test with that of the untreated control batch (mc). The index of curative activity is evaluated by calculating the percentage inhibition (I) according to the formula:

$$I = \frac{mc - m}{mc} \times 100$$

The compounds of the invention showed a significant inhibitory effect with respect to the formation of the edema. The results of the test are shown in Table I.

TABLE I

| COMPOUND | DOSE mg·kg$^{-1}$ | I |
|---|---|---|
| Example 2 (hydrochloride) | 166 | −34% (p < 0.05) |
| Example 3 (hemitartrate) | 200 | −26% (p < 0.01) |
| Example 4 (monophosphate) | 173 | −28% (p < 0.05) |
| Example 6 (monophosphate) | 160 | 0 35% (p < 0.01) |

EXAMPLE 23

Inhibition of the Degradation Reaction of Cyclic AMP by Phosohodiesterase

The enzyme extract necessary for this study is prepared from rat brain.

After decapitation, the brain is removed, weighed and frozen for half an hour at −70° C. The preparation, maintained in ice, is then diluted and homogenized in 50% glycerol containing 50 mmol tris(hydroxymethyl)aminomethane and 50 mmol magnesium sulfate, in the proportion of 5 ml per gram of brain. The preparation is then centrifuged. The supernatent is distributed in aliquots and stored at 4° C.

In the study, the enzyme extract is incubated in the presence of cyclic AMP (Boehringer ® Ref. 102300), alkaline phosphatase (Boehringer ® Ref 108138), adenosine deaminase (Boehringer ® Ref. 102091) and increasing amounts of the compounds of the invention. The kinetics of the degradation of cyclic AMP is followed by spectrophotometry at 25° C. A mixture devoid of alkaline phosphatase and adenosine deaminase is used as blank. The measurement of the optical density is carried out at 265 nm. The concentration of the compounds of the invention leading to a 50% inhibition of the enzymatic reaction (IC$_{50}$) is calculated. Two reference substances, diosmine and theoprylline, are studied according to the same methodology.

The results of this study, seen in Table II, showed that the products of the invention are very powerful inhibitors of the degredation reaction of cyclic AMP by phosphodiesterase, and confirm the importance of their uses in therapy. In effect, it is known that the release of the biochemical mediators of inflammation, such as histamine, leukotrienes, lysosomal enzymes and free radicals, is inhibited by an increase in the intracellular concentration of cyclic AMP [Kaliner M., Austen K. F., "Bioch. Pharmacol", (1974) 23, p.763–771 and Lehmeyer J. E., Johnston R. B. Jr., "Clin. Immunol. Immunopathol", (1978), 9 p. 482–490]. The products of the invention, by inhibiting the degradation reaction of cyclic AMP, increase its intracellular concentration and contribute to the decrease in the release of the biochemical mediators of inflammation. It should be noted that the products of the invention possess an inhibitory activity that is much larger in comparison with the products customarily used as a reference: theophylline and diosmine.

TABLE II

| COMPOUND | IC$_{50}$ (M) |
|---|---|
| Example 2 | 2.0 × 10$^{-5}$ |
| Example 3 | 2.5 × 10$^{-5}$ |
| Example 7 | 1.0 × 10$^{-5}$ |
| Example 8 | 5.7 × 10$^{-5}$ |
| DIOSMINE | 10 × 10$^{-5}$ |
| THEOPHYLLINE | 100 × 10$^{-5}$ |

EXAMPLE 24

Evaluation of the Pharmacodynamic Activity with Respect to Oxygen-Containing Free Radicals Produced by Polymorphonuclear Leukocytes The possible pharmacodynamic activity of the compounds of the invention with respect to the production of free radicals by polymorphonuclear leukocytes was investigated in vitro. The cellular model used was rat polymorphonuclear leukocytes. This model is capable of producing free radicals in a manner that can be monitored. The production of free radicals was quantified by measurement of the chemiluminescence, which is proportional to their quantity.

Quantities of $2 \times 10^6$ polymorphonuclear leukocyte cells, isolated from heparinized rat blood, are mixed with solutions of increasing concentrations of the compounds of the invention ($2 \times 10^{-4}$M to $2 \times 10^{-8}$M). Appropriate amounts of Hanks' solution, Zymosan ® (Sigma 24250) and Luminol ® (Merck 82007) are then added successively. The solutions are kept shielded from the light, and transferred rapidly to a liquid scintillation counter. In the "blank" sample, the polymorphonuclear leukocytes are replaced by an equivalent volume of Hanks' solution, and in the "control" sample, the solution of "test compounds" is replaced by a Hanks' solution. The same study was carried out with a reference product: diosmine.

The percentage inhibition of free radical production was calculated by the following formula:

$$\% \text{ inhibition} = 100\% - \left[ \frac{Cl\ \text{control} - Cl\ \text{compounds}}{Cl\ \text{control} - Cl\ \text{blank}} \right]$$

Cl control: Maximum chemiluminescence of "control" sample

Cl compounds: Maximum chemiluminescence of "test compounds" sample

Cl blank: Maximum chemiluminescence of "blank" sample

The concentrations of the compounds of the invention and of diosmine that produce a 50% inhibition (IC$_{50}$) of the chemiluminescence reaction are given in Table III.

The accumulation of oxygen-containing free radicals in the extracellular medium is known to represent a threat to cell and tissue integrity [Bruce, A. et al. Lab. Invest., (1982), 47, (5), p. 412–426]. In effect, oxygen metabolites are involved in tissue inflammation reactions, both at vascular level and as regards the attack at tissue and cell level.

The products of the invention, by inhibiting the formation of oxygen-containing free radicals, prevent the formation and maintenance of edema, which is a manifestation of venous insufficiency (Phlebology 85, Eds. D. Negus and G. Jantet, 1986, John Libley Lon. Par).

TABLE III

| COMPOUND | $IC_{50}$ |
|---|---|
| DIOSMINE | $40 \times 10^{-6}$ M |
| EXAMPLE 2 | $4 \times 10^{-6}$ M |
| EXAMPLE 6 | $10 \times 10^{-6}$ M |
| EXAMPLE 8 | $15 \times 10^{-6}$ M |

EXAMPLE 25

Coated Tablets Containing a 400-mg Dose of 3'-[2-{4-[(2,3,4-Trimethoxyphenyl)methyl]-1-Piperazinyl}-2-Oxoethoxy]-4'-Methoxy-5-Hydroxyflavone 7-Rhamnoglucoside (T.M.P.M.P.F.R.)

| T.M.P.M.P.F.R. | 400.000 mg |
|---|---|
| Sodium carboxymethylstarch | 27.000 mg |
| Microcrystalline cellulose | 62.000 mg |
| White beeswax | q.s. waxing |
| Gelatin | 31.000 mg |
| Glycerol | 0.426 mg |
| Hydroxypropylmethylcellulose | 7.078 mg |
| Sodium lauryl sulfate | 0.034 mg |
| Yellow iron oxide | 0.166 mg |
| Red iron oxide | 0.055 mg |
| Titanium oxide | 1.362 mg |
| Polyethylene glycol 6000 | 0.453 mg |
| Magnesium stearate | 4.426 mg |
| Talc | 6.000 mg |
| for one coated tablet. | |

We claim:

1. A compound of the formula I:

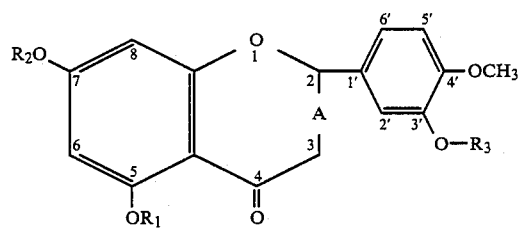

in which:

A is a single or double bond, $R_1$ and $R_3$, which may be identical or different, are each a hydrogen atom, an alkoxycarbonylmethylene radical of formula $-CH_2CO_2R_4$ (in which $R_4$ denotes an alkyl radical having 1 to 5 carbon atoms) or a radical of formula W:

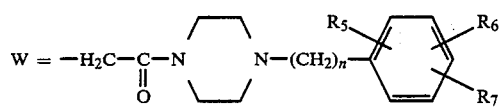

(in which n is equal to 0 or 1 and $R_5$, $R_6$ and $R_7$, which may be identical or different, are each a hydrogen or halogen atom, a hydroxyl radical, a trifluoromethyl radical, a lower alkyl radical containing 1 to 5 carbon atoms or an alkoxy radical containing 1 to 5 carbon atoms), $R_2$ is a hydrogen atom, an alkoxycarbonylmethylene radical of formula $-CH_2CO_2R_4$, a radical of formula W, or a β-glucose or rutinose molecule linked to the oxygen to which it is attached with a glycoside bond, on condition, however, that at least either $R_1$ or $R_2$ or $R_3$ is a radical of formula W, and their addition salts with a pharmaceutically acceptable inorganic or organic acid.

2. Compound of claim 1 being 3'-[2-{4-[(2,3,4-Trimethoxyphenyl)methyl]-1-piperazinyl}-2-oxoethoxy]-4'-methoxy-5-hydroxyflavone 7-rhamnoglucoside, or an addition salt thereof, with a pharmaceutically acceptable inorganic or organic acid.

3. Compound of claim 1 being 3'-[2-{4-[(2,3,4-Trimethoxyphenyl)methyl]1-piperazinyl}-2-oxoethoxy]-4'-methoxy-5,7-dihydroxy-flavone, or an addition salt thereof with a pharmaceutically acceptable inorganic or organic acid.

4. A process for preparing the compounds of formula I, as claimed in claim 1, wherein:

either:

diosmine, the compound of formula II:

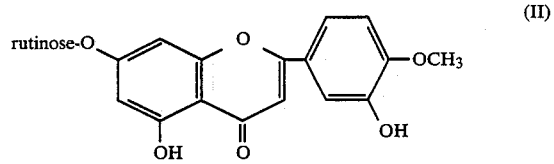

is reacted with an alkyl chloride of formula III containing the compounds of formulae IIIa and IIIb:

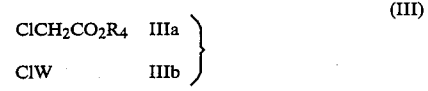

in which $R_4$ and W have the same meanings as for the formula I, as claimed in claim 1, in a polar nitrogenous organic solvent, in the presence of an acidic inorganic salt of an alkali metal, at a temperature of between 80° and 120° C., either to obtain, with the compounds of formula IIIa, the compounds of formula IV:

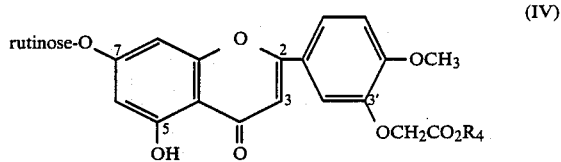

in which $R_4$ has the meaning stated for the formula I, as claimed in claim 1, which is subjected to an acid hydrolysis in the presence of a concentrated inorganic acid and at a temperature of between 35° and 55° C. to form the compound of the formula V:

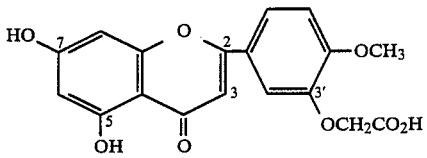

(V)

which is then:
either:

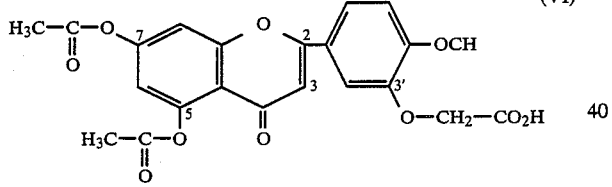

subjected to an acetylation by means of acetic anhydride in a basic nitrogenous organic solvent and at room temperature to form the compound of formula VI:

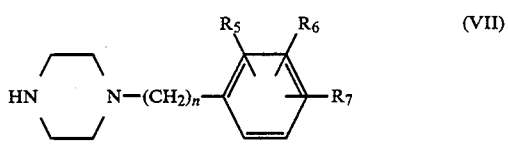

(VI)

which is reacted with a piperazine derivative of formula VII:

(VII)

in which n, $R_5$, $R_6$ and $R_7$ have the same meaning as for the formula I, as claimed in claim 1, in the presence of a low molecular weight tertiary amine and ethyl chloroformiate, at a temperature of between 0° and 20° C., to form the compounds of formula VIII:

in which n, $R_5$, $R_6$ and $R_7$ have the meaning stated for the formula I, as claimed in claim 1,
which is then subjected to a deacetylation in solution in dimethylformamide in the presence of an acidic inorganic salt of an alkali metal at a temperature of between 80° and 120° C., to form the compounds of formula $I_A$:

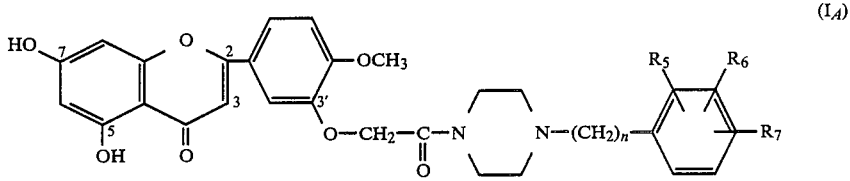

($I_A$)

in which the meaning of n, $R_5$, $R_6$ and $R_7$ remains identical to that given for the formula I, as claimed in claim 1, which is condensed with a compound of formula III to form compounds of formula $I_B$:

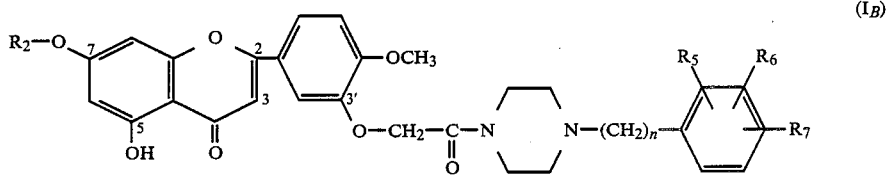

($I_B$)

in which n, $R_5$, $R_6$ and $R_7$ have the meaning stated above and $R_2$ is an alkoxycarbonylmethylene radical of the formula —$CH_2CO_2R_4$ or a radical of formula W, as claimed in claim 1,
or:
esterified with a primary or secondary alcohol containing from 1 to 5 carbon atoms, in an anhydrous medium at a temperature of between 80° and 110° C. and in the presence of p-toluenesulfonic acid, to form the compounds of formula IX:

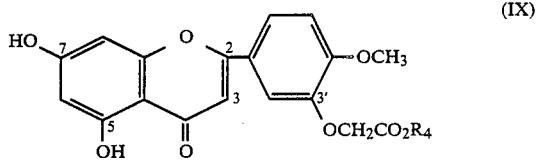

(IX)

in which $R_4$ has the same meaning as for the formula IV, which is reacted
either with an alkyl chloride of formula IIIb to form the compounds of formula $I_C$:

(VIII)

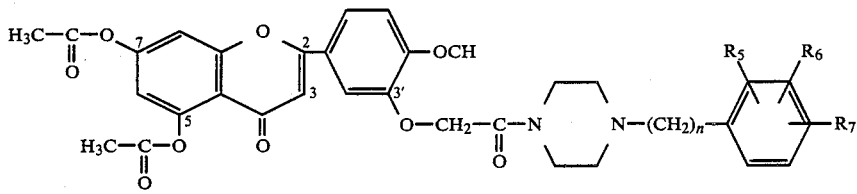

(IC)

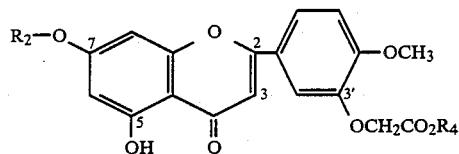

in which $R_2$ denotes a radical of formula W, as claim in claim 1,
or with an alkyl chloride of formula IIIa to form the compounds of formula X:

(X)

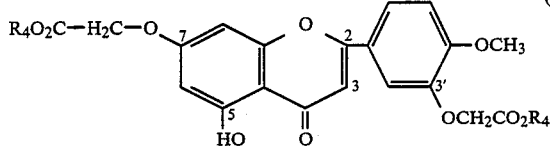

in which $R_4$ has the meaning stated above for the formula I, as claimed in claim 1,
which is condensed with the compound of formula IIIb, to obtain the compounds of formula $I_D$:

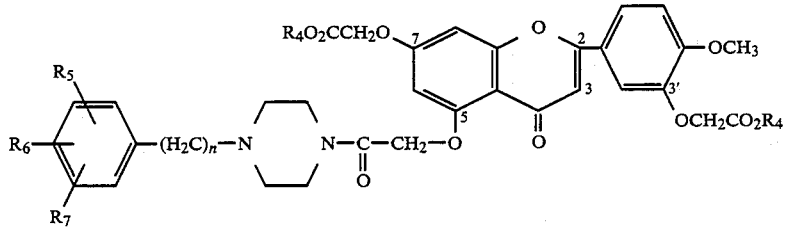

in which the meaning of n, $R_4$, $R_5$, $R_6$ and $R_7$ remains identical to that given for the formula I, as claimed in claim 1,
or to obtain,
with the compounds of formula IIIb, the compounds of general formula $I_E$, in which n, $R_5$, $R_6$ and $R_7$ have the meaning stated for the formula I, as claimed in claim 1,
which is then subjected to an enzymatic hydrolysis by means of naringinase to form the compounds of general formula $I_F$:

(IF)

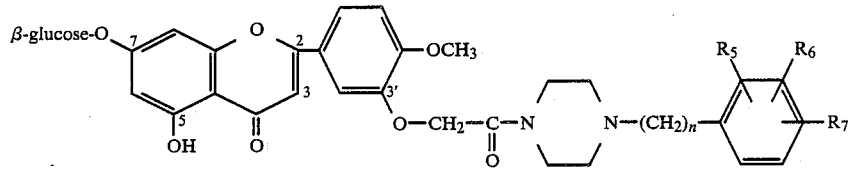

in which n, $R_5$, $R_6$ and $R_7$ have the meaning stated above,
which are then,
subjected to an enzymatic hydrolysis by means of β-glucosidase to form the compounds of general formula $I_4$,
which are then condensed with a compound of general formula III to form the compound of general formula $I_B$, or:

a compound of general formula XI:

(XI)

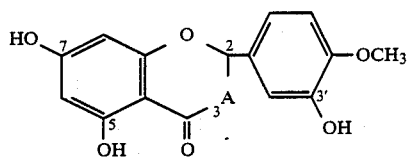

in which A was the same meaning as for the formula I, as claimed in claim 1, is reacted with a suitable amount of the compounds of the general formula IIIb,
to form the compounds of formula $I_G$:

(IE)

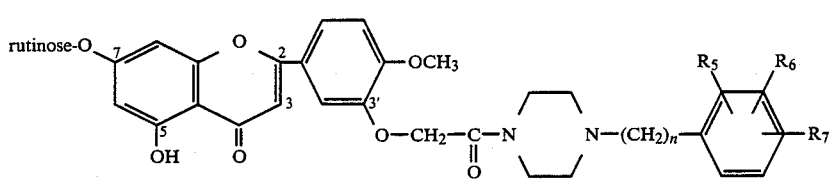

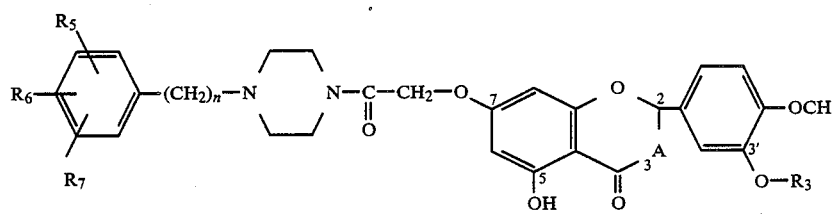

(I_G)

in which n, A, $R_5$, $R_6$ and $R_7$ have the meaning stated in the formula I, as claimed in claim 1, and $R_3$ Is a hydrogen atom when the amount of the compounds of formula IIIb used is approximately equimolar, or a radical of the formula W, as claimed in claim 1, when the alkylation is performed with at least double the amount of alkyl chloride of formula III$_b$, and wherein the compounds of the Formulae $I_A$ to $I_G$, which collectively form the compounds of the formula I, as claimed in claim 1, are then salified, if desired, with a pharmaceutically acceptable organic or inorganic acid.

5. A pharmaceutical composition containing, as active principle, a compound as claimed in claim 1, in combination or mixed with a pharmaceutically acceptable, non-toxic, inert vehicle or excipient.

6. The pharmaceutical composition as claimed in claim 5, containing the active principle at a dose of 50 to 500 mg.

7. A method of treating vascular conditions in a subject in need thereof comprising the step of administering to the said subject an amount of a compound of claim 1 which is effective for the said purpose.

8. The method of claim 7 wherein the vascular condition is selected from chronic venous insufficiency, edema of the lower limbs, and hemorrhoidal disease.

9. The method of claim 1 wherein the compound is administered at a dose of 50 to 500 mg.

* * * * *

UNITED STATES PATENT AND TRADEMARK OFFICE
CERTIFICATE OF CORRECTION

PATENT NO. : 4,970,301

DATED : Nov. 13, 1990

INVENTOR(S) : Yves Rolland, Jacques Duhault

It is certified that error appears in the above-identified patent and that said Letters Patent is hereby corrected as shown below:

Title Page, [75] Inventors:, line 2; "DuHault," should read
   --Duhault, --. (Decl. & Power of Attorney)
Column 4, approximately line 26; move "(VIII)" below the upper
   formula down to approximately line 35 below the lower formula.
Column 6, approximately line 15; move "(XI)" down to approximately
   line 22.
Column 6, approximately line 32; move "($I_E$)" down to approximately
   line 40.
Column 7, line 54; "9 p." should read -- 9, p. --.
Column 8, line 46; "-3'-O-" should read -- 3'-O- --.
Column 10, line 24; "-oxoethoxy-]-" should read -- -oxoethoxy]- --.
Column 12, approximately line 29; "1piperazinyl" should read
   -- 1-piperazinyl --.
Column 12, line 51; "-oxoethoxy   -4'" should read
   -- -oxoethoxy]-4' --.
Column 14, line 19; "-methoxy--5" should read -- -methoxy-5 --.
Column 14, line 45; "s" should read -- is --.
Column 15, line 43; "C. after" should read -- C. After --.
Column 15, line 62; "511m/z;" should read -- 511 m/z; --.
Column 16, line 62; "glycerol 913" should read
   -- glycerol. 913 --.
Column 22, line 24; "d 1H;" should read -- d, 1H; --.
Column 22, line 65; "soectrum" should read -- spectrum --.
Column 25, line 29, second occurrence at end of line;
   "-1-" should read -- -2- --.
Column 27, line 54; "theoprylline," should read -- theophylline,--.
Column 27, line 67; "9p." should read -- 9, p. --.
Column 30, approximately line 17; "methyl]1" should read
   -- methyl]-1 --.

UNITED STATES PATENT AND TRADEMARK OFFICE
CERTIFICATE OF CORRECTION

PATENT NO. : 4,970,301
DATED : Nov. 13, 1990
INVENTOR(S) : Yves Rolland, Jacques Duhault It is certified that error appears in the above-identified patent and that said Letters Patent is hereby corrected as shown below:

Column 31, approximate line 38, right hand corner of formula "OCH" should read -- $OCH_3$ --.

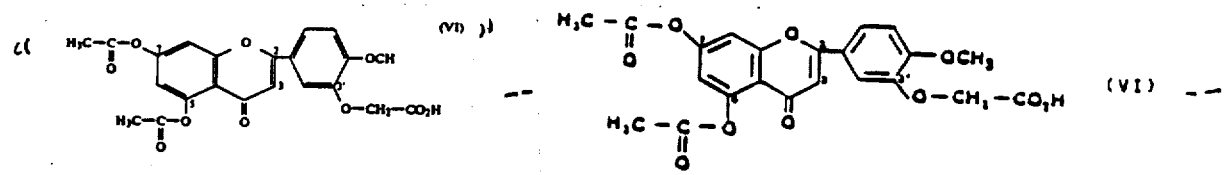

Column 31, last formula, middle of formula "OCH" should read -- $OCH_3$ --.

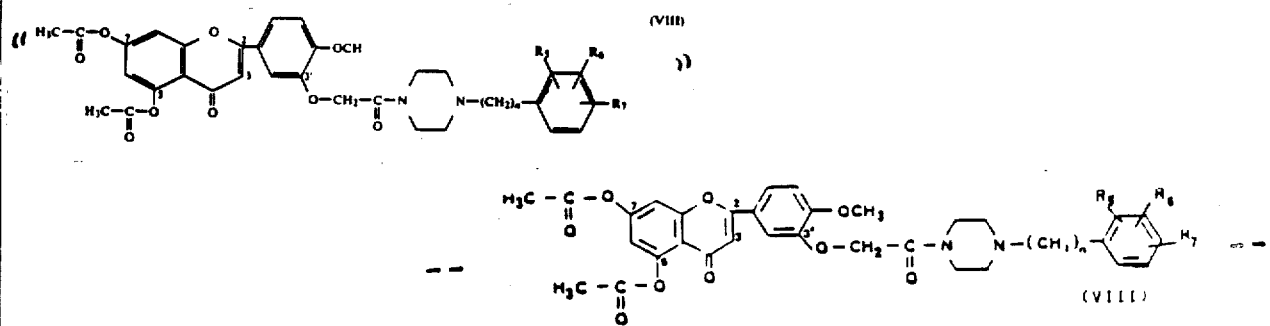

UNITED STATES PATENT AND TRADEMARK OFFICE
CERTIFICATE OF CORRECTION

PATENT NO. : 4,970,301
DATED : Nov. 13, 1990
INVENTOR(S) : Yves Rolland, Jacques Duhault It is certified that error appears in the above-identified patent and that said Letters Patent is hereby corrected as shown below:

Column 34, line 54; "A was" should read -- A has --.
Column 35, approximately line 13; "$R_3$ Is" should read -- $R_3$ is --.
Column 36, claim 9, line 1; "claim 1" should read -- claim 7 --.

Signed and Sealed this

Twenty-third Day of June, 1992

Attest:

DOUGLAS B. COMER

Attesting Officer

Acting Commissioner of Patents and Trademarks